US010864086B2

(12) United States Patent
Weiman

(10) Patent No.: US 10,864,086 B2
(45) Date of Patent: *Dec. 15, 2020

(54) EXPANDABLE INTERVERTEBRAL SPACER AND METHOD OF POSTERIOR INSERTION THEREOF

(71) Applicant: GLOBUS MEDICAL, INC., Audubon, PA (US)

(72) Inventor: Mark Weiman, Downingtown, PA (US)

(73) Assignee: Globus Medical, Inc.

( * ) Notice: Subject to any disclaimer, the term of this patent is extended or adjusted under 35 U.S.C. 154(b) by 65 days.

This patent is subject to a terminal disclaimer.

(21) Appl. No.: 15/884,493

(22) Filed: Jan. 31, 2018

(65) Prior Publication Data

US 2018/0147064 A1 May 31, 2018

Related U.S. Application Data

(63) Continuation of application No. 13/763,012, filed on Feb. 8, 2013, now Pat. No. 9,913,726, which is a continuation of application No. 13/031,313, filed on Feb. 21, 2011, now Pat. No. 8,394,145.

(60) Provisional application No. 61/307,659, filed on Feb. 24, 2010.

(51) Int. Cl.
*A61F 2/44* (2006.01)
*A61F 2/30* (2006.01)

(52) U.S. Cl.
CPC .......... *A61F 2/442* (2013.01); *A61F 2/4455* (2013.01); *A61F 2002/30523* (2013.01); *A61F 2002/30556* (2013.01); *A61F 2002/30579* (2013.01)

(58) Field of Classification Search
CPC .......... A61F 2/44; A61F 2/442; A61F 2/4425; A61F 2/4455; A61F 2/446; A61F 2/4465; A61F 2/447; A61F 2/4611; A61F 2002/4475
See application file for complete search history.

(56) References Cited

U.S. PATENT DOCUMENTS

| | | | |
|---|---|---|---|
| 4,349,921 A | 9/1982 | Kuntz | |
| 4,599,086 A | 7/1986 | Doty | |
| 4,863,476 A | 9/1989 | Shepperd | |
| 4,863,477 A | 9/1989 | Monson | |
| 5,123,926 A | 6/1992 | Pisharodi | |
| 5,290,312 A | 3/1994 | Kojimoto et al. | |
| 5,306,310 A | 4/1994 | Siebels | |
| 5,375,823 A | 12/1994 | Navas | |

(Continued)

FOREIGN PATENT DOCUMENTS

| | | |
|---|---|---|
| CA | 2088066 A1 | 1/1992 |
| DE | 4012622 C1 | 7/1991 |

(Continued)

*Primary Examiner* — Kevin T Truong
*Assistant Examiner* — Tracy L Kamikawa

(57) ABSTRACT

An expandable intervertebral spacer has a plurality of arms. The arms can be retracted or extended. The spacer has a width that is narrower than the width between the nerve roots near the posterior approach to an intervertebral space. Once inserted into the intervertebral space, the arms can be deployed. The deployed arms expand the height and width of the spacer. Once deployed, the spacer stabilizes two adjacent vertebrae. The arms are interconnected mechanically to deploy simultaneously.

12 Claims, 5 Drawing Sheets

(56) References Cited

U.S. PATENT DOCUMENTS

| | | |
|---|---|---|
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 6,039,761 A | 3/2000 | Li et al. |
| 6,045,579 A | 4/2000 | Hochschuler et al. |
| 6,080,193 A | 6/2000 | Hochschuler et al. |
| 6,099,531 A | 8/2000 | Bonutti |
| 6,126,689 A | 10/2000 | Brett |
| 6,176,882 B1 | 1/2001 | Biedermann et al. |
| 6,258,125 B1 | 7/2001 | Paul et al. |
| 6,562,074 B2 | 5/2003 | Gerbec et al. |
| 6,576,016 B1 | 6/2003 | Hochschuler et al. |
| 6,554,863 B2 | 8/2003 | Paul et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 7,985,256 B2 | 7/2011 | Grotz et al. |
| 8,070,813 B2 | 12/2011 | Grotz et al. |
| 8,123,810 B2 | 2/2012 | Gordon |
| 8,192,495 B2 | 6/2012 | Simpson et al. |
| 8,303,663 B2 | 11/2012 | Jimenez et al. |
| 8,377,140 B2 | 2/2013 | DeFalco et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,647,386 B2 | 2/2014 | Gordon |
| 8,696,751 B2 | 4/2014 | Ashley et al. |
| 8,771,360 B2 | 7/2014 | Jimenez et al. |
| 8,894,710 B2 | 11/2014 | Simpson et al. |
| 8,932,355 B2 | 1/2015 | Grotz et al. |
| 8,940,049 B1 | 1/2015 | Jimenez et al. |
| 8,956,413 B2 | 2/2015 | Ashley et al. |
| 8,992,620 B2 | 3/2015 | Ashley et al. |
| 9,028,550 B2 | 5/2015 | Shulock et al. |
| 9,358,125 B2 | 6/2016 | Jimenez et al. |
| 9,532,883 B2 | 1/2017 | McLuen et al. |
| 9,622,878 B2 | 4/2017 | Grotz |
| 9,913,726 B2 * | 3/2018 | Weiman ............ A61F 2/4455 |
| 2002/0045945 A1 | 4/2002 | Liu |
| 2004/0049271 A1 | 3/2004 | Biedermann |
| 2004/0054412 A1 | 3/2004 | Gerbec et al. |
| 2004/0087947 A1 | 5/2004 | Lim et al. |
| 2004/0153065 A1 | 8/2004 | Lim |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0049590 A1 * | 3/2005 | Alleyne ............ A61F 2/442 |
| | | 623/17.11 |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish, Jr. et al. |
| 2006/0058878 A1 | 3/2006 | Michelson |
| 2006/0122701 A1 | 6/2006 | Kister |
| 2006/0129244 A1 | 6/2006 | Ensign |
| 2006/0142859 A1 * | 6/2006 | McLuen ............ A61F 2/4455 |
| | | 623/17.11 |
| 2006/0149385 A1 | 7/2006 | McKay |
| 2006/0195192 A1 | 8/2006 | Gordon et al. |
| 2006/0229729 A1 | 10/2006 | Gordon |
| 2006/0253201 A1 | 11/2006 | McLuen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0140207 A1 | 6/2008 | Olmos et al. |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0125062 A1 | 5/2009 | Arnin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292316 A1 * | 11/2009 | Hess ............ A61B 17/7065 |
| | | 606/249 |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2011/0035007 A1 * | 2/2011 | Patel ............ A61F 2/4611 |
| | | 623/17.11 |
| 2012/0277861 A1 | 11/2012 | Steele et al. |
| 2013/0274883 A1 | 10/2013 | McLuen et al. |
| 2014/0088714 A1 | 3/2014 | Miller et al. |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0166396 A1 | 6/2016 | McClintock |

(56) References Cited

U.S. PATENT DOCUMENTS

2016/0324654 A1   11/2016  Loebl et al.
2017/0100258 A1    4/2017  Jimenez et al.
2017/0119543 A1    5/2017  Dietzel et al.

FOREIGN PATENT DOCUMENTS

| DE | 4327054 C1 | 4/1995 |
| EP | 0576379 B1 | 6/1993 |
| EP | 0610837 B1 | 7/1994 |
| EP | 3111896 A1 | 1/2017 |
| SU | 1424826 A1 | 9/1988 |
| WO | 9201428 A1 | 2/1992 |
| WO | 9525485 A1 | 9/1995 |

* cited by examiner

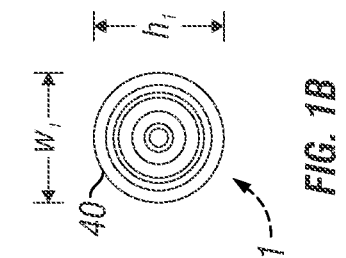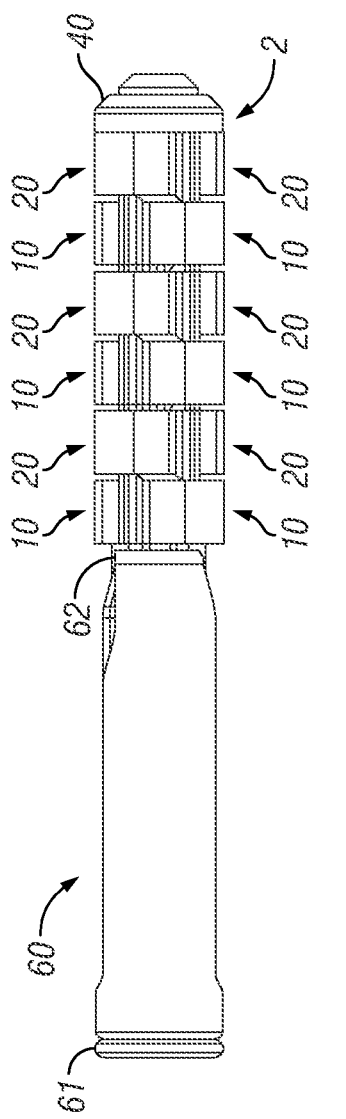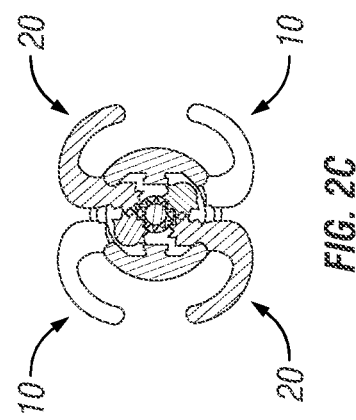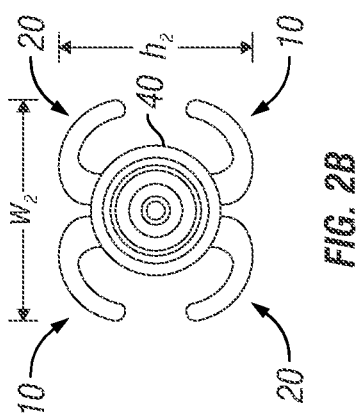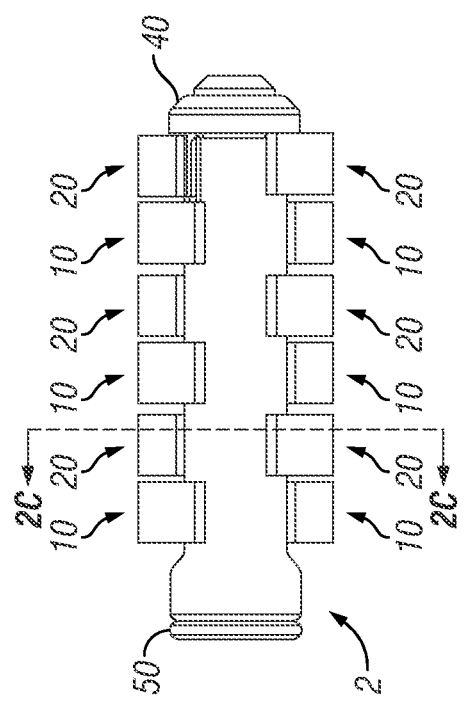

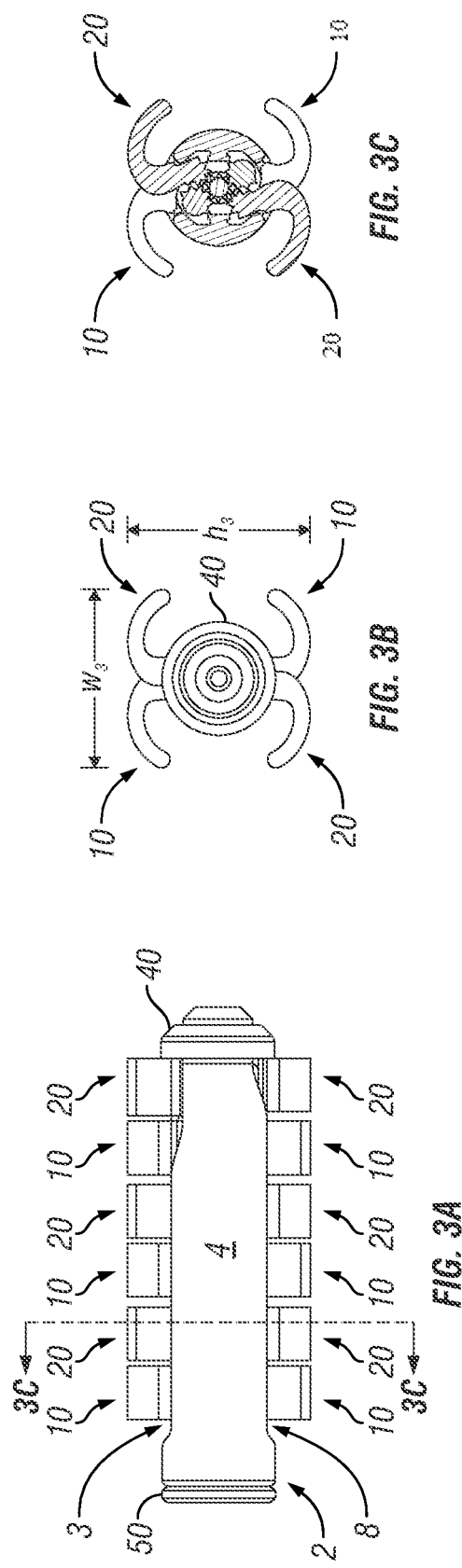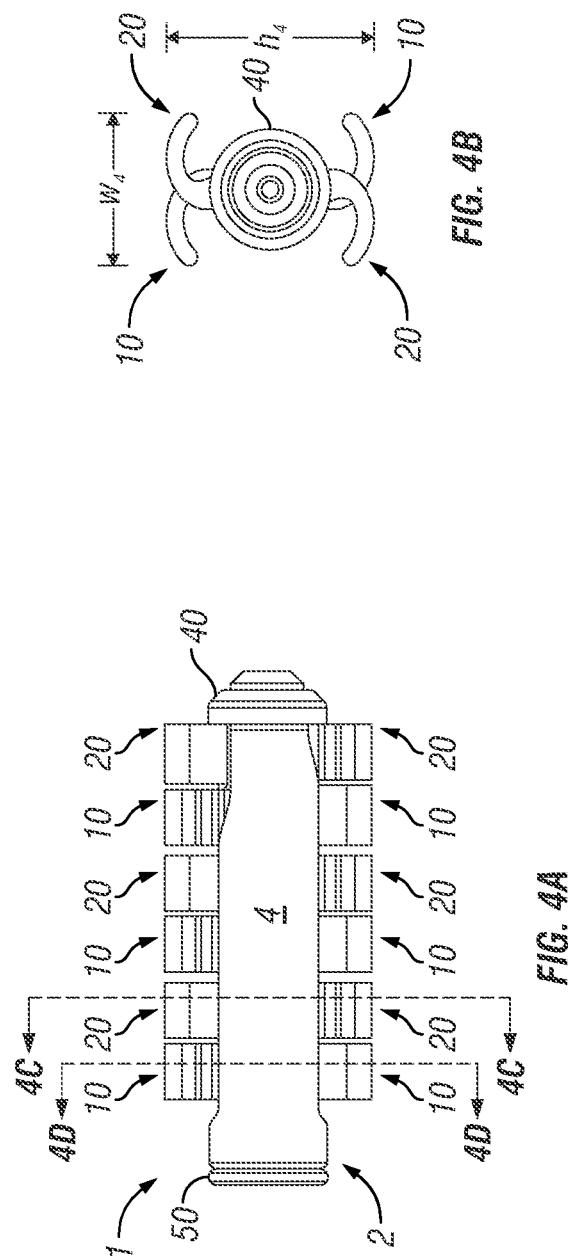

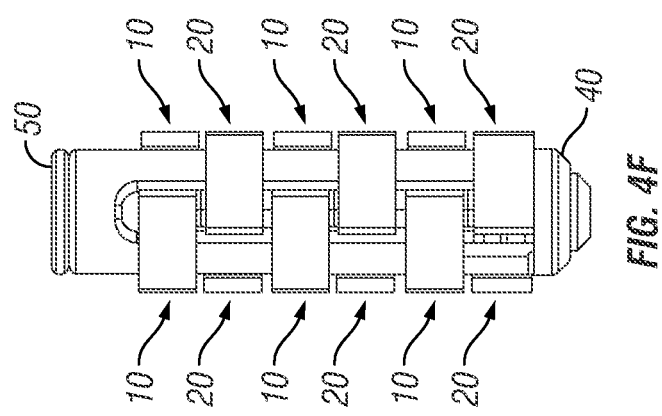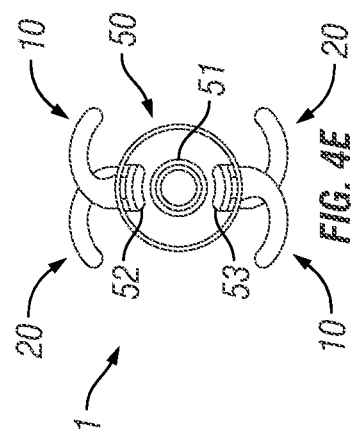

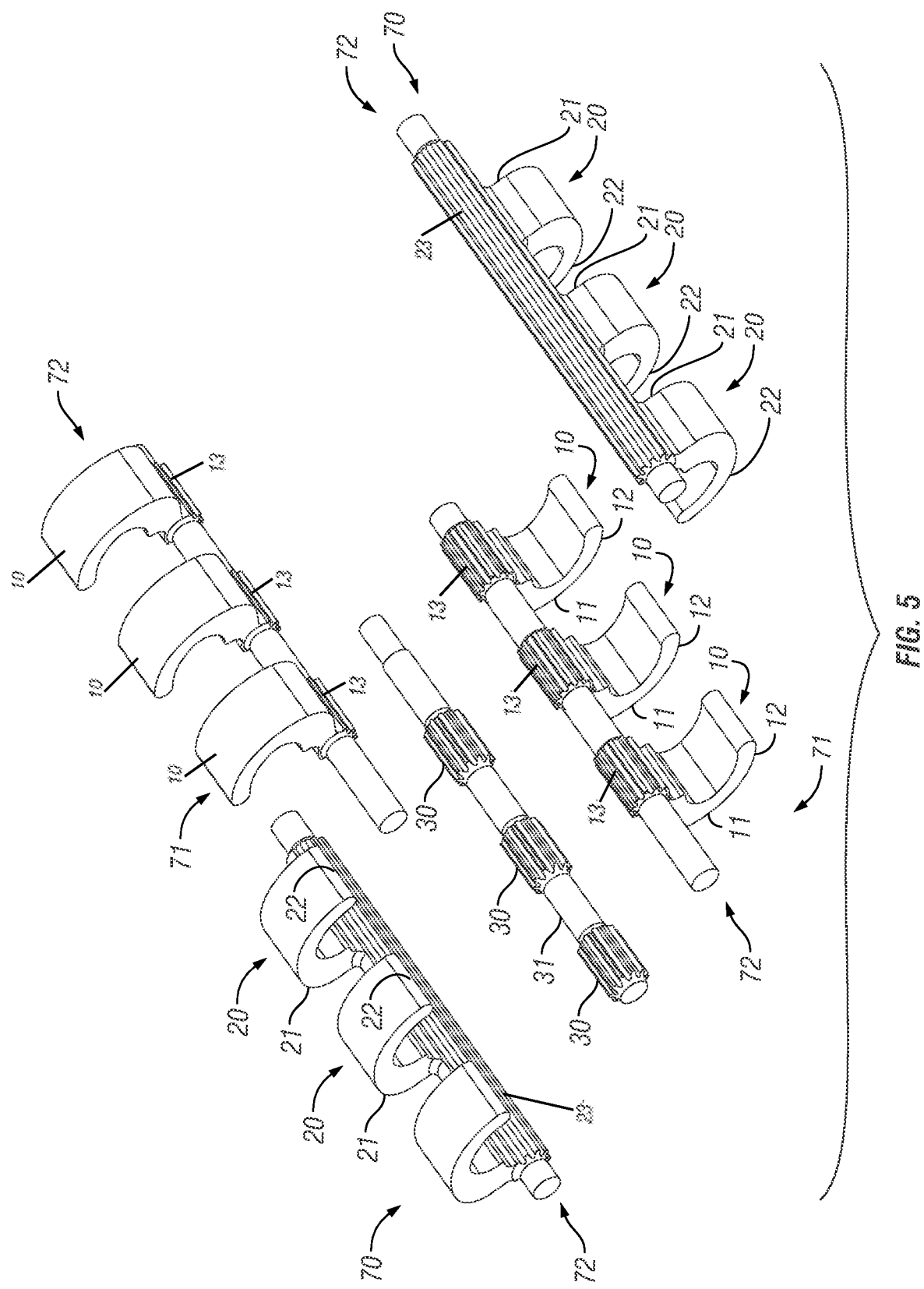

EXPANDABLE INTERVERTEBRAL SPACER AND METHOD OF POSTERIOR INSERTION THEREOF

CROSS-REFERENCE TO RELATED APPLICATIONS

This application is a continuation of U.S. patent application Ser. No. 13/763,012, filed Feb. 8, 2013, which is a continuation of U.S. patent application Ser. No. 13/031,313, filed Feb. 21, 2011, now U.S. Pat. No. 8,394,145, which claims priority to U.S. Provisional Application No. 61/307,659, filed Feb. 24, 2010, which are incorporated by reference herein in their entireties for all purposes.

FIELD OF THE INVENTION

The present disclosure generally relates to intervertebral spacers and surgical methods for inserting intervertebral spacers, in particular, insertion via a posterior approach.

BACKGROUND OF THE INVENTION

The spine includes a series of joints routinely called motion segment units, which are the smallest component of the spine that exhibits kinematic behavior characteristic of the entire spine. The motion segment unit is capable of flexion, extension, lateral bending, and translation. The components of each motion segment unit include two adjacent vertebrae and their apophyseal joints, the intervertebral disc, and the connecting ligamentous tissue. Each component of the motion segment unit contributes to the mechanical stability of the joint.

Components of a motion segment that move out of position or become damaged can lead to serious pain and may lead to further injury to other components of the spine. Depending upon the severity of the structural changes that occur, treatment may include fusion, discectomy, or laminectomy.

Underlying causes of structural changes in the motion segment unit leading to instability include trauma, degeneration, aging, disease, surgery, and the like. Thus, rigid stabilization of one or more motion segment units may be an important element of a surgical procedure in certain cases (i.e., injuries, deformities, tumors, etc.), whereas it is a complementary element in others (i.e., fusion performed due to degeneration). The purpose of rigid stabilization is the immobilization of a motion segment unit.

FIG. 6 shows the anatomy of a typical vertebra 100. The vertebra 100 includes a vertebral body 101. An intervertebral disc 130 is supported by the vertebral body 101. The intervertebral disc 130 includes a disc annulus 131 surrounding nucleus pulposus 132. The vertebra includes number of processes: the transverse process 102, superior articular process 103, inferior articular process 104, and the spinous process 105. The transverse process 102 includes an anterior tubercle 106 and a posterior tubercle 107. The transverse process 102 has a foramen transversium 108 formed therein. The vertebra 100 has a foramen 109 formed therein. The spinal cord 120 runs vertically in the foramen 109. The meninges 121 surrounds the spinal cord 120. Within the spin cord 120, gray matter 122 is surrounded by white matter 123. Nerve roots 124 exit the spinal cord 120 and descend laterally. The nerve roots 124 partially cover a posterior approach to the vertebral body 101. Each nerve root includes a dorsal root 125 and ventral root 126.

As mentioned above, current surgical techniques typically involve fusing one or more unstable motion segment units and possibly, the removal of ligaments, bone, disc, or combinations thereof included in the unstable motion segment unit or units prior to fusing. There are several disadvantages to fusion, however. For example, the fusing process results in a permanent or rigid internal fixation of all or part of the intervertebral joints and usually involves the implantation of metallic rods, plates, and the like for stabilization. In all cases, the systems are intended to rigidly immobilize the motion segment unit to promote fusion within that motion segment unit.

When inserting a prosthesis into an intervertebral space via a posterior approach, the nerve roots can be damaged. These nerve roots from the adjacent vertebra are spaced apart at a distance narrower than the width of the intervertebral disc. The nerve roots block the posterior of the intervertebral space. To insert a prosthesis that is as wide as the intervertebral disc, the nerve roots are retracted.

Vertically expandable intervertebral prostheses are known. Most of these devices employ mechanical means to expand their height. The device is placed into an intervertebral space and then expanded vertically to support the adjacent vertebrae.

SUMMARY OF THE INVENTION

According to one aspect of the invention, an expandable intervertebral spacer for posterior approach to an intervertebral space without needing retraction of a nerve root is provided. The spacer has a body and at least one rotatable extension. The rotatable extension will be hereafter referred to as "arm". The body has a width that is narrow enough to fit between the nerve roots at the posterior entrance to an intervertebral space. The arm or arms retract within the body when the spacer is being passed between the nerve roots. The arm or arms are then deployed once the body has passed between the nerve roots into the intervertebral space. The arm or arms increase the overall height and width of the spacer when the arm or arms are deployed. The overall height of the spacer is adjusted to stabilize the adjacent vertebrae relative to each other. The expanding overall width of the spacer provides a broader base upon which the vertebrae are stabilized.

The spacer can include a plurality of arms. Deploying L-shaped arms from a superior and inferior surface of the body has been found by the inventors to be an advantageous way to provide a spacer that is narrow enough to fit between the nerve roots and that can expand after being inserted to be wide enough to provide a stable base. Deploying the L-shaped arms also allows the spacer to expand enough vertically to fill the intervertebral space. Deploying some of the L-shaped arms by rotating them clockwise and others counterclockwise provides a useful way to expand the width of the spacer from both sides. Providing a spacer with arms that alternate between clockwise rotating arms and counterclockwise rotating arms along a depth (i.e. posterior to anterior) of the spacer has been found to provide a particularly stabile spacer. The number of arms along the depth of the spacer can be adjusted depending on the depth of the intervertebral space and the patient's anatomy. An implant with six pairs (i.e. superior and anterior) of arms has been found to provide a particularly stabile spacer.

The arms are generally L-shaped. The arms can include a relatively short rotatable extensions connected to the spacer body that end with a relatively long extension that compliments the body surface when retracted. The arms have an axis of rotation. The axis of rotation is eccentric from the center of the body of the spacer. The arms have a cam extending from the axis of rotation. A contact surface for providing a stable abutment with the adjacent vertebra is connected to the cam. As the arm rotates on the eccentric axis, the contact surface extends beyond the perimeter (i.e. the circumference in a cylindrical embodiment) of the body.

It has been found to be advantageous to configure the arm so that it is short enough to be fully retracted within the body when retracted and long enough to extend beyond the body when deployed. To create this configuration, a furthest distance on the arm from the axis of rotation of the arm should be greater than the shortest distance from the axis of rotation to the perimeter of the body in the plane of rotation of the arm. A furthest distance on the arm from the axis of rotation should be less than a furthest distance on the perimeter of the body in a given plane of rotation of the arm.

The arms are generally L-shaped. The contact surfaces of the arms can be curved to complement the perimeter of the body of the spacer when the arms are retracted. By complementing the shape of the body, the arms when retracted provide a narrow cross section that can be passed between the posterior nerve roots of an intervertebral space.

The spacer includes a means for deploying two or more arms simultaneously in the spacer in a same rotational direction. At least two arms may be configured advantageously to rotate in the same plane of rotation. A respective arm gear is formed around the axis of rotation of each arm. A central gear is intermeshed between both arm gears. When the central gear is rotated, then both arm gears rotate in order to deploy both arms. So that both arms rotate in the same direction (i.e. both clockwise or both counterclockwise), the arm gears are not directly intermeshed with each other.

The spacer includes a means for deploying two arms simultaneously in the spacer in different rotational directions. A respective arm gear is formed around the axis of rotation of each arm. The arm gear of the first arm directly (i.e. without an intervening gear) engages the arm gear of the second arm. When deploying the arms, one of the arms will rotate clockwise while the other arm rotates counterclockwise. The first arm and the second arm can be found at different depths axially (i.e. posterior to anterior). The arm gear or gears of at least one of the arms can reach to a deeper depth to intermesh with the other arm gear. A central gear can be added to turn the first arm gear. The central gear can be configured not to enmesh directly with the second arm gear. The central gear does not enmesh directly with gears at every other depth because the rotations direction in which the arms rotate alternates at alternating depths.

The two means for deploying the arms can be combined to produce a spacer in which two arms deploy simultaneously in one rotational direction at a given depth and two arms deploy simultaneously in an opposite direction at a different depth. A central gear is enmeshed with two arm gears of two arms at a given depth of the spacer. The arm gears at the first depth enmesh with arm gears of two additional arms at a different depth. When the central gear is turned, all four arms rotate to deploy or retract.

The arms can be disposed depthwise (i.e. posterior to anterior) along the spacer in order to provide a spacer that is both compact in size in the retracted state and that is stabile in the deployed state. The arms can be disposed in pairs at given depths along the spacer. Both arms at a given depth rotate in the same direction (both clockwise or both counterclockwise). To maximize the length of the arm while allowing the arm to retract fully, the axes of rotation of each arm in the pair can be disposed on opposite sides of the central gear. The pairs of arms at adjacent depths can open in the opposite direction to the opening direction at the given depth. In other words, the arms alternate depthwise clockwise, then counterclockwise.

The spacer is sized so that the overall width of the body with the arms retracted is narrower than a space between nerve roots blocking a posterior approach to an intervertebral space to be filled by the spacer. In this way, the spacer can be inserted into the intervertebral space by moving it between the nerve roots without needing to retract the nerve roots. Once the spacer is inserted into the intervertebral space, the arm or arms can be deployed to expand the overall width of the spacer to a width greater than the space between the nerve roots.

The overall height of the spacer (i.e. the body plus arms) when the arms are displaced is configurable to match a height of the intervertebral space to be filled. The overall height is configured by controlling the amount that arms are deployed. The height may not exactly match the height of the intervertebral disc being replaced because the disc may be damaged or compressed. Because the actual desired height might be different than the actual height of the disc, the height approximates the desirable height of the intervertebral disc being replaced. When the arms are in the retracted position, the height of the spacer may be smaller than the height of the intervertebral space. Once the spacer is inserted in the intervertebral space, the arms can be deployed to expand the height. When the arms are deployed, the arms operate to support the adjacent vertebrae.

When deployed, the spacer can have an overall width that approximates the width of the body of the vertebrae being stabilized. As discussed, when the arms are retracted the overall width of the spacer should be less than the space between the nerve roots along the posterior approach to the intervertebral space. However, once the spacer is inserted into the intervertebral space, the arms can be deployed. The arms not only expand vertically as discussed previously. The arms can spread horizontally to approximate the width of the body of the vertebrae being stabilized. By being wider, a more stable connection is formed between the implant and the vertebrae.

The depth (i.e. posterior to anterior length) of the space can approximate a depth of the intervertebral disc to be replaced. By having a depth that matches the depth of the disc being replaced, a stable connection between the spacer and the adjacent vertebrae can be established. In spacers having a longer depth, the number of arms along the length can be increased. In spacers having a shorter depth, the number of arms along the length can be decreased.

The body of the expandable intervertebral spacer can have a slot, in particular, a superior slot and/or an inferior slot formed in the body. The arms can extend from within the body through the slots to outside the body. The mechanism such as the parts can be contained by the body yet the arms can still extend through the slots.

A method of using the spacer for stabilizing a first vertebra relative to a second vertebra via a posterior approach has the advantage that the nerve roots along with posterior of the intervertebral space do not need to be retracted. A first step of the method involves forming an incision to a posterior of an intervertebral space. The next step involves inserting an expandable intervertebral spacer in a retracted position into the intervertebral space. The intervertebral spacer has a height and width less than a distance between nerve root stems at the posterior of the intervertebral space. The next step is expanding a width and height of the expandable intervertebral spacer to a width wider than the distance between the nerve root stems and/or a height approximating a height of an intervertebral disc being replaced.

The spacer can be implanted endoscopically. That is, an endoscopic tube can be inserted in the incision to allow the spacer to be moved from outside the patient to the intervertebral space via the endoscopic tube.

BRIEF DESCRIPTION OF THE DRAWINGS

FIG. 1A is a diagrammatic right side view of an expandable intervertebral spacer and insertion tool according to the invention where the expandable intervertebral spacer is in a retracted position.

FIG. 1B is a front view of the expandable intervertebral spacer shown in FIG. 1A.

FIG. 2A is right side view of the expandable intervertebral spacer shown in FIG. 1A with the expandable intervertebral spacer in a first state of expansion.

FIG. 2B is front side view of the expandable intervertebral spacer shown in FIG. 2A.

FIG. 2C is a front sectional view of the expandable intervertebral spacer shown in FIG. 2A taken along line B-B in FIG. 2A.

FIG. 3A is right side view of the expandable intervertebral spacer shown in FIG. 1A with the expandable intervertebral spacer in a second state of expansion.

FIG. 3B is a front side view of the expandable intervertebral spacer shown in FIG. 3A.

FIG. 3C is a front sectional view of the expandable intervertebral spacer shown in FIG. 3A taken along line B-B in FIG. 3A.

FIG. 4A is a right side view of the expandable intervertebral spacer shown in FIG. 1A with the expandable intervertebral spacer in a third state of expansion.

FIG. 4B is a front side view of the expandable intervertebral spacer shown in FIG. 4A.

FIG. 4C is front section view of the expandable intervertebral spacer shown in FIG. 4A taken along line B-B in FIG. 4A.

FIG. 4D is a front section view of the expandable intervertebral spacer shown in FIG. 4A taken along line A-A in FIG. 4A.

FIG. 4E is rear side view of the expandable intervertebral spacer shown in FIG. 4A.

FIG. 4F is a top view of the expandable intervertebral spacer shown in FIG. 4A.

FIG. 5 is a partial perspective exploded view of the intervertebral spacer shown in FIGS. 1-4.

DETAILED DESCRIPTION OF THE ILLUSTRATED EMBODIMENTS

Figure 6:
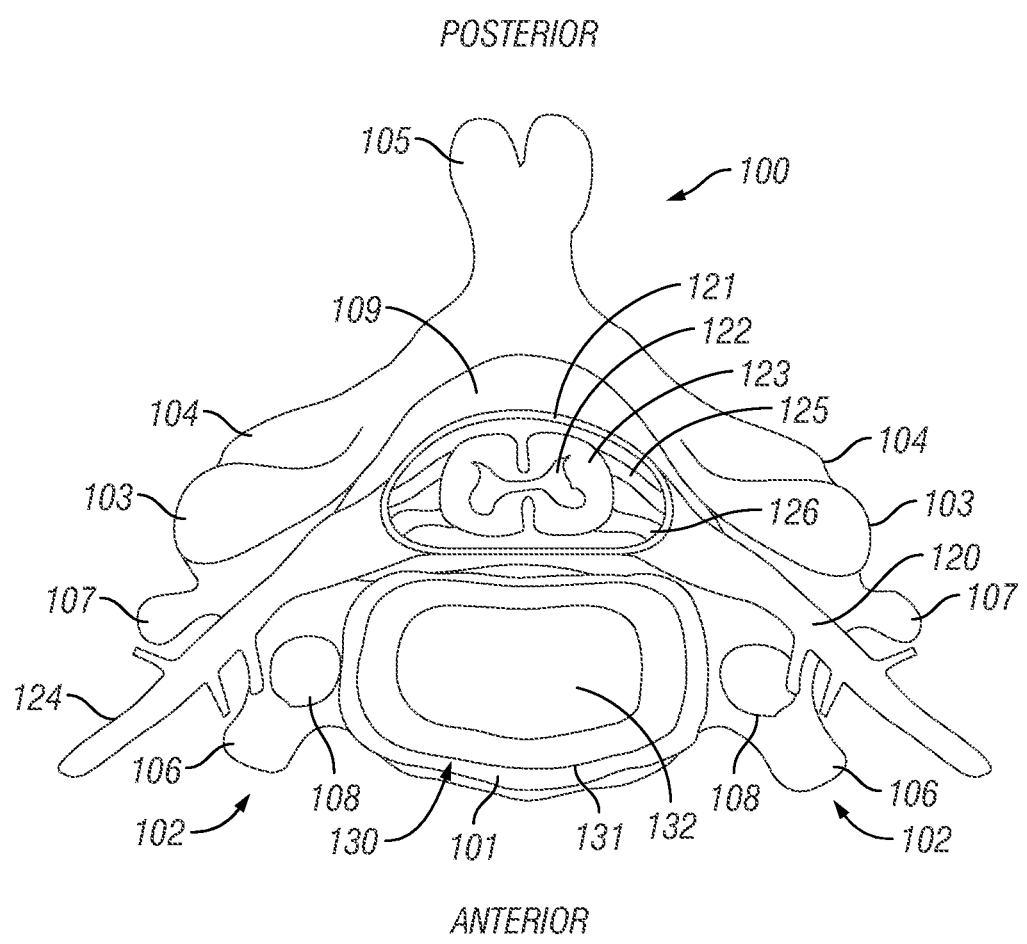
FIG. 6 is a diagrammatic top sectional view of a vertebra.

Referring now to the figures of the drawing in detail, there is seen an expandable intervertebral spacer 1. The expandable intervertebral spacer 1 is typically inserted in a retracted state as shown in FIGS. 1A-1B into an intervertebral space. Once inserted into the intervertebral space, a width w and height h of the expandable intervertebral spacer 1 can be expanded as shown in FIGS. 2A-4F. The construction and operation of the expandable intervertebral spacer 1 are detailed below.

The expandable intervertebral spacer 1 includes a cylindrical body 2. The body 2 has a right side surface 4 and a left side surface 5. A superior slot 3 is formed in the body 2 at a superior position on the wall of the body 2. An inferior slot 8 is formed in the body 2 at an inferior position on the wall of the body 2. Arms 10, 20 deploy through the inferior and superior slots 3 and 8. As seen in FIG. 4D, the left and right side surfaces 4 and 5 have fins 6 and 7 formed on an inner surface of the cylindrical body 2 to strengthen the body 2, to key or align arms 10, 20, and additional to prevent arms 10, 20 from splaying, or bending sideways, particularly under a load.

In an embodiment, four arm assemblies 70, 70, 71, and 71 extend from the body 2. The arm assemblies 70 and 71 are shown in FIG. 5. Each arm assembly 70, 71 has an axis of rotation 72. Each arm assembly 70, 71 rotates about its respective axis of rotation 72. An arm gear 13 is formed about each axis of rotation 72 on the counterclockwise extending arm assemblies 71. An arm gear 23 is formed about each axis of rotation 72 on the clockwise extending arm assemblies 70. Three counterclockwise arms 10 are included in each counterclockwise arm assembly 71. Each counterclockwise arm 10 has a cam 11 extending from the arm gear 13. A contact surface 12 is formed on each cam 11 at an end of the cam 11 opposing the arm gear 13. Likewise, three clockwise arms 20 are included in each clockwise arm assembly 70. Each of the clockwise arms 20 has a cam 21 extending from the arm gear 23. A contact surface 22 is formed on each cam 21 at an end of the cam opposing the arm gear 23. The arms 10 of a counterclockwise extending arm assembly 71 are spaced to intermesh with the spaced arms 20 of a clockwise extending arm assembly 70.

The counterclockwise arm assembly 71 intermeshes with the clockwise arm assembly 72. The arms 20 of the clockwise extending arm assembly 70 have a width measured from a posterior position to an anterior point. The width of the arms 20 is less than the spacing between the arms 10 on the counterclockwise extending arm assembly 71. Preferably, the width of the arms 20 is nearly as wide as the spacing between the arms 10 on the counterclockwise extending arm assembly 71. The arms 10 of the counterclockwise extending arm assembly 71 have a width measured from a posterior position to an anterior point. The width of the arm 10 is no greater than the spacing between the arms 20 on the clockwise extending arm assembly 70. Preferably, the width of the arms 10 is nearly as wide as the spacing between the arms 20 on the clockwise extending arm assembly 70.

A central axle 31 extends lengthwise inside the body 2. The central axle 31 has three central gears 30 formed around the central axle 31 at different depths of the central axle 31. In the embodiment shown, the central gears 30 are at depths to intermesh with arm gears 13 of the counterclockwise arm 10; see FIG. 4D. The central axle 31 has no gears at depths where the central gears 30 would intermesh with arm gears 23 of the clockwise arm 20; see FIGS. 2C, 3C, and 4C.

The arm gear 13 of the counterclockwise arm 10 engages the arm gear 23 of the clockwise arm 20 that extends through the same slot 3 or 8. FIGS. 2C, 3C, and 4C show the arm gears 13 engaged with the arm gears 23.

As shown in FIG. 4D, when the central axle 31 is rotated, the central gear 30 rotates. Central gear 30 turns the arm gear 13. As the arm gear 13 turns, the counterclockwise arm 10 moves (i.e. deploys or retracts). As shown in FIGS. 2C, 3C, and 4C, as the arm gear 13 turns, the clockwise arm 20 turns in an opposite direction as the counterclockwise arm 10.

In an alternate embodiment, which is not shown in the figures, the central gears 30 intermesh with the arm gears 23 of the clockwise arm 20 but not the arm gears 13 of counterclockwise arm 10.

As shown in FIG. 4D, the central gears 30 intermesh with the arm gears 13. As a result, when the central axle 31 is turned clockwise, the counterclockwise arm assemblies rotate counterclockwise. As the counterclockwise arm assemblies rotate clockwise, the arms 10, extend outwards, through the slots 3 and 8, in a direction away from a central longitudinal axis of spacer 1.

The axes of rotation 72 of the counterclockwise arms 10 and the clockwise arms 20 are eccentric from the central axle 31. The arms 10 and 20, by rotating on eccentric axes, move relative to the center of the body when the arms 10 and 20 are rotated.

The arms 10 and 20 have cams 11 and 21, respectively. The cams 11 and 21 extend laterally from the respective axes of rotation. Contact surfaces 12 and 22 are disposed on the ends of the cams 11 or 12, respectively. The contact surfaces 12 and 22 are configured to contact the body of the adjacent vertebrae when extended. The contact surfaces are at an angle with the cams so that the contact surfaces form a stable contact with the adjacent vertebra.

The arms 10 and 20 deploy (i.e. extend beyond the perimeter of the body 2) and retract (i.e. extend no farther than the perimeter of the body 2) from the body 2. FIGS. 1A and 1B show the arms 10 and 20 in a retracted position. FIGS. 2A, 2B, and 2C show the arms 10 and 20 in a slightly deployed position. FIGS. 3A, 3B, and 3C show the arms 10 and 20 in a medium deployed position. FIGS. 4A, 4B, 4C, 4D, 4E, and 4F show the arms 10 and 20 in a fully deployed position. A slightly deployed position is rotationally closer to the retracted position than the fully deployed position; the term does not necessarily reflect the amount of the arm 10 or 20 that is extending beyond the body 20

To be able to fully retract against the body 2, the arms 10 and 20 have a length from the respective axis 72 to a furthest point on the arm 10 or 20 that is no greater than the distance from the given axle 72 to the furthest edge of the body 2. The width of the arm, vis-à-vis the length of the cam 11 or 21, does not extend wider than the body 2 when the arm 10 or 20 is retracted.

To be able to extend, the arms 10 and 20 are longer than the distance from axis of rotation to the perimeter of the body 2. More particularly, the arms 10 and 20 a furthest distance on the arm from its respective axis 72 is longer than the shortest distance from the axis 72 to the nearest edge of the body 2.

As seen in FIG. 1B, the spacer 1 has a circular cross section. FIG. 1A shows that the spacer 1 has a generally cylindrical shape when in a retracted position. To aid in insertion, the distal end 40 has a frustoconical shape. Embodiments with other inclined, ramped, or sloping distal surfaces are also possible.

FIG. 1B shows a front view of the spacer 1 with the arms 10 and 20 retracted. The overall height is h1 and the width is w1. FIG. 2B shows the spacer 1 with the arms 10 and 20 in a slightly deployed position. In FIG. 2B, the spacer 1 has a height h2 and width w2. The height and width are greater in FIG. 2B than FIG. 1B (i.e. h2>h1 and w2>w1). FIG. 3B show the spacer 1 with the arms 10 and 20 in a medium deployed position. In the medium deployed position, the height h3 and width w3 are greater than the height h1 and width w1 in the retracted position shown in FIG. 1B (i.e. h3>h1 and w3>w1). In the medium deployed position, the height h3 is greater than the height in slightly deployed position h2 and the width w3 is narrower than the width in the slightly deployed position w2 (i.e. h3>h2 and w3<w2). FIG. 4B shows the spacer 1 with the arms 10 and 20 in a fully deployed position. In the fully deployed position, the height h4 is the greatest (i.e. h4>h3>h2>h1). In the fully deployed position, the width w4 is greater than the initial width w1 but not as wide as the other widths (i.e. h2>h3>h4>h1).

FIGS. 1A, 2A, 3A, and 4A show side views of the spacer 1. As the arms 10 and 20 deploy, the arms extend through the superior slot 3 and inferior slot 8, which are both formed in the body 2. Along the length of the spacer 1, the arms 10 alternate with arms 20.

FIG. 4E shows the proximal end 50 the spacer 1. Sockets 52 and 53 are formed in the proximal end 50 to aid in attaching a tool 60 during insertion and/or removal of the spacer 1. A receptacle 51 is formed in the proximal end 50. A tool 60 is insertable in the receptacle 51 to operate the central gear 30 in order to retract or deploy the arms 10 and 20 of the device.

FIG. 1A shows a tool 60 attached to the spacer 1. The tool 60 has a connector 62 on its distal end. The connector 62 inserts in the sockets 52 and 53 in the proximal end 50 of the spacer 1. The connector 62 holds the spacer 1 in place rotationally with respect to the tool 60. The tool 60 allows the spacer 1 to be inserted via an endoscopic tube leading from outside the patient to the intervertebral space that is to be filled. A knob 61 on the proximal end of the tool 60 can be rotated relative to the rest of the tool 60 to turn the central gear 30 of the spacer 1. The central gear 30 is accessed through the port 51 and engages the tool connector 62 through a mating engagement, such as a hex connection or the like.

The spacer 1 is sized to have a width w1 in a retracted position that is narrower than the space between nerve roots stems extending near the posterior entrance to an intervertebral space. Because the spacer 1 is narrower than the space between the nerve roots, the nerve roots do not need to be retracted, displaced, or disturbed during insertion. Once in the intervertebral space, the central gear 30 is operated to deploy the arms 10 and 20 of the spacer 1. The deployed arms 10 and 20 have a width w that is typically wider than the space between the nerve roots. The spacer 1 is adjusted until the overall height h of the spacer 1 fills the height of the invertebral space and properly supports the adjacent vertebrae.

A method of using the spacer 1 is the following. First, an incision is made in a patient to the posterior of the intervertebral space that is to be stabilized. Next, an endoscopic tube is inserted in the incision from outside the patient to the intervertebral space. A spacer 1 is seated on a tool 60. The spacer/tool assembly is then inserted via the endoscopic tube to the intervertebral space. The spacer 1 is inserted between the nerve roots near the intervertebral space while the spacer 1 is in a retracted position. The knob 61 on the proximal end of the tool 60 is rotated to turn the central gear 30 in the spacer 1 relative to the body 2. The body 2 remains stationary relative to the tool 61 during relative movement of the arms 10 and 20. As the central gear 30 is rotated counterclockwise while looking from the distal position (i.e. FIG. 4D), the counterclockwise arms 10 rotate clockwise to deploy. In turn, the arm gears 13 of the counterclockwise arms 10 engage the arm gears 23 of the clockwise arms 20 and cause the clockwise arm 20 to rotate counterclockwise to deploy. In this way, turning the central gear 30 causes both sets of arms 10 and 20 to deploy. The arms 10 and 20 are deployed until the spacer 1 has an overall height h equal to the intervertebral space being filled and the adjacent vertebrae are stable. The tool 60 is separated from the spacer 1 and removed via the endoscopic tube from the patient. In embodiments, that are not shown, the spacer 1 is further stabilized by screws and plates that secure the spacer 1 to adjacent vertebrae.

The spacer 1 can be removed by performing the following steps. An incision is made to a proximal side of the intervertebral space where the spacer 1 is installed. An endoscopic tube or cannula is delivered via the incision to the intervertebral space. Stabilizers such as screws and plates that connect the spacer 1 to anatomy are disconnected. The central gear 30 is turned clockwise (as seen by looking from the distal view in FIG. 4D). The arms 10 and 20 retract into the body 2. The spacer 1 is passed between the nerve roots on the proximal side of the intervertebral space while the spacer 1 is in the retracted position. A replacement stabilizer may then be inserted into the intervertebral space.

While it is apparent that the invention disclosed herein is well calculated to fulfill the objects stated above, it will be appreciated that numerous modifications and embodiments may be devised by those skilled in the art.

All references cited herein are expressly incorporated by reference in their entirety. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. An expandable intervertebral implant comprising:
a cylindrical body extending along a longitudinal axis and having a plurality of slots;
a central axle extending through the cylindrical body along the longitudinal axis; and
a first arm assembly comprising a plurality of first curved arms and a second arm assembly comprising a plurality of second curved arms, wherein when the central axle is rotated, the plurality of first and second curved arms are configured to deploy through the plurality of slots such that a width and a height of the expandable implant is expanded,
wherein each of the first curved arms has a first proximal end and a first distal tip and each of the second curved arms has a second proximal end and a second distal tip,
wherein each of the first curved arms is configured to concavely curve extending from the first proximal end to the first distal tip, and each of the second curved arms is configured to concavely curve extending from the second proximal end to the second distal tip, and
wherein the central axle engages the first proximal end of each first curved arm without engaging the second proximal end of each second curved arm,
wherein the central axle includes a plurality of central gears.

2. The expandable intervertebral implant according to claim 1, wherein the first arm assembly includes a first arm gear at each first proximal end, and each first arm gear engages one of the plurality of central gears of the central axle.

3. The expandable intervertebral implant according to claim 2, wherein the second arm assembly includes a second arm gear, and the second arm gear of the second arm assembly engages at least one first arm gear of the first arm assembly.

4. The expandable intervertebral implant according to claim 1 further comprising a third arm assembly comprising a plurality of third curved arms.

5. The expandable intervertebral implant according to claim 4 further comprising a fourth arm assembly comprising a plurality of fourth curved arms.

6. The expandable intervertebral implant according to claim 1, wherein the plurality of first curved arms rotate in a first direction, and the plurality of second arms rotate in a second direction.

7. The expandable intervertebral implant according to claim 1, wherein the plurality of first curved arms rotate in a first direction, and the plurality of second arms rotate in a second direction opposite the first direction.

8. An expandable intervertebral implant comprising:
a cylindrical body extending along a longitudinal axis and having a plurality of slots;
a central axle extending through the cylindrical body along the longitudinal axis; and
a first arm assembly comprising a plurality of first curved arms, a second arm assembly comprising a plurality of second curved arms, a third arm assembly comprising a plurality of third curved arms, and a fourth arm assembly comprising a plurality of fourth curved arms, wherein when the central axle is rotated, the plurality of first, second, third, and fourth curved arms are configured to deploy through the plurality of slots such that a width and a height of the expandable implant is expanded,
wherein each of the first curved arms has a first proximal end and a first distal tip and each of the second curved arms has a second proximal end and a second distal tip, and
wherein each of the first curved arms is configured to concavely curve extending from the first proximal end to the first distal tip, and each of the second curved arms is configured to concavely curve extending from the second proximal end to the second distal tip, and
wherein the central axle engages the first proximal end of each first curved arm without engaging the second proximal end of each second curved arm,
wherein the central axle includes a plurality of central gears.

9. The expandable intervertebral implant according to claim 8, wherein the first arm assembly includes a first arm gear at each first proximal end, and each first arm gear engages one of the plurality of central gears of the central axle.

10. The expandable intervertebral implant according to claim 9, wherein the second arm assembly includes a second arm gear, and the second arm gear of the second arm assembly engages at least one first arm gear of the first arm assembly.

11. The expandable intervertebral implant according to claim 8, wherein the plurality of first curved arms rotate in a first direction, and the plurality of second arms rotate in a second direction.

12. The expandable intervertebral implant according to claim 8, wherein the plurality of first curved arms rotate in a first direction, and the plurality of second arms rotate in a second direction opposite the first direction.

\* \* \* \* \*